United States Patent [19]
Porter et al.

[11] Patent Number: 5,094,110
[45] Date of Patent: Mar. 10, 1992

[54] CROSS STRETCH MEASURING SYSTEM

[75] Inventors: Richard M. Porter, Hartsville, S.C.; Gilbert L. Horton, Kernersville, N.C.; Herman M. Respess, Tobaccoville, N.C.; Eddie D. Poole, Lexington, N.C.; Terri L. McBride, Walkertown, N.C.; William A. Borst, Burlington, N.C.

[73] Assignee: Sara Lee Corporation, Winston-Salem, N.C.

[21] Appl. No.: 615,020

[22] Filed: Nov. 16, 1990

[51] Int. Cl.5 .............................................. G01N 3/08
[52] U.S. Cl. ...................................................... 73/832
[58] Field of Search ................. 73/159, 788, 789, 826, 73/832, 837, 860

[56] References Cited
U.S. PATENT DOCUMENTS

| | | |
|---|---|---|
| 1,817,617 | 8/1931 | Gosch . |
| 2,187,914 | 1/1940 | Reitan . |
| 3,039,299 | 6/1962 | Roof . |
| 3,400,576 | 9/1968 | Siciliano . |
| 3,444,728 | 5/1969 | Burns .................................... 73/832 |
| 3,879,990 | 4/1975 | Joy ........................................ 73/159 |
| 3,975,956 | 8/1976 | Peel . |
| 4,137,763 | 2/1979 | Swallow . |
| 4,866,991 | 9/1989 | Tse ....................................... 73/837 |

Primary Examiner—Robert Raevis

[57] ABSTRACT

In a system for measuring the cross stretch along selected areas of a tubular portion of a hosiery article to determine whether the degree of stretch falls within selected parameters, a pair of arms having designated arcuate portions over which a selected area of the article to be tested is positioned. A fluid cylinder displaces a first arm relative to a second arm to stretch the selected area of the article and therefore apply a force to the second arm. When a prescribed force is reached, a control means, in response to a signal from a load cell coupled to the second arm, records the linear displacement of the first arm and reverses the operation of the fluid cylinder.

7 Claims, 8 Drawing Sheets

CROSS STRETCH MEASURING SYSTEM

This invention relates generally to the art of testing hosiery articles such as hosiery blanks, stockings, pantyhose, etc.

The system is used to apply a predetermined pressure or force to designated areas of a tubular portion of an article to be tested to determine the amount of cross stretch or elongation of the hosiery fabric in the test areas. The designated areas may include the panty portion of a blank or garment, the upper knee, the knee, the foot, the toe, and the area where the panty portion joins the leg portion.

The apparatus is particularly adapted for use in repeated testing of various segments of an elongated tubular hosiery article.

It is an object of the invention to provide a highly reliable and accurate system for determining the elastic cross stretch characteristics of a hosiery article for ensuring "fit".

Another object of the invention is the provision of a system for testing the cross stretch or elongation of various designated areas of an elongated hosiery which does not destroy the hosiery being tested by exceeding the elastic limits.

Still another object of the invention is the provision of a safety mechanism for preventing non-designated areas of the hosiery article from applying a force to the testing system.

Other objects and advantages of the invention will appear from the following description of the invention explained by way of example only with reference to the accompanying drawings.

DETAILED DESCRIPTION OF THE INVENTION

Figure 1:
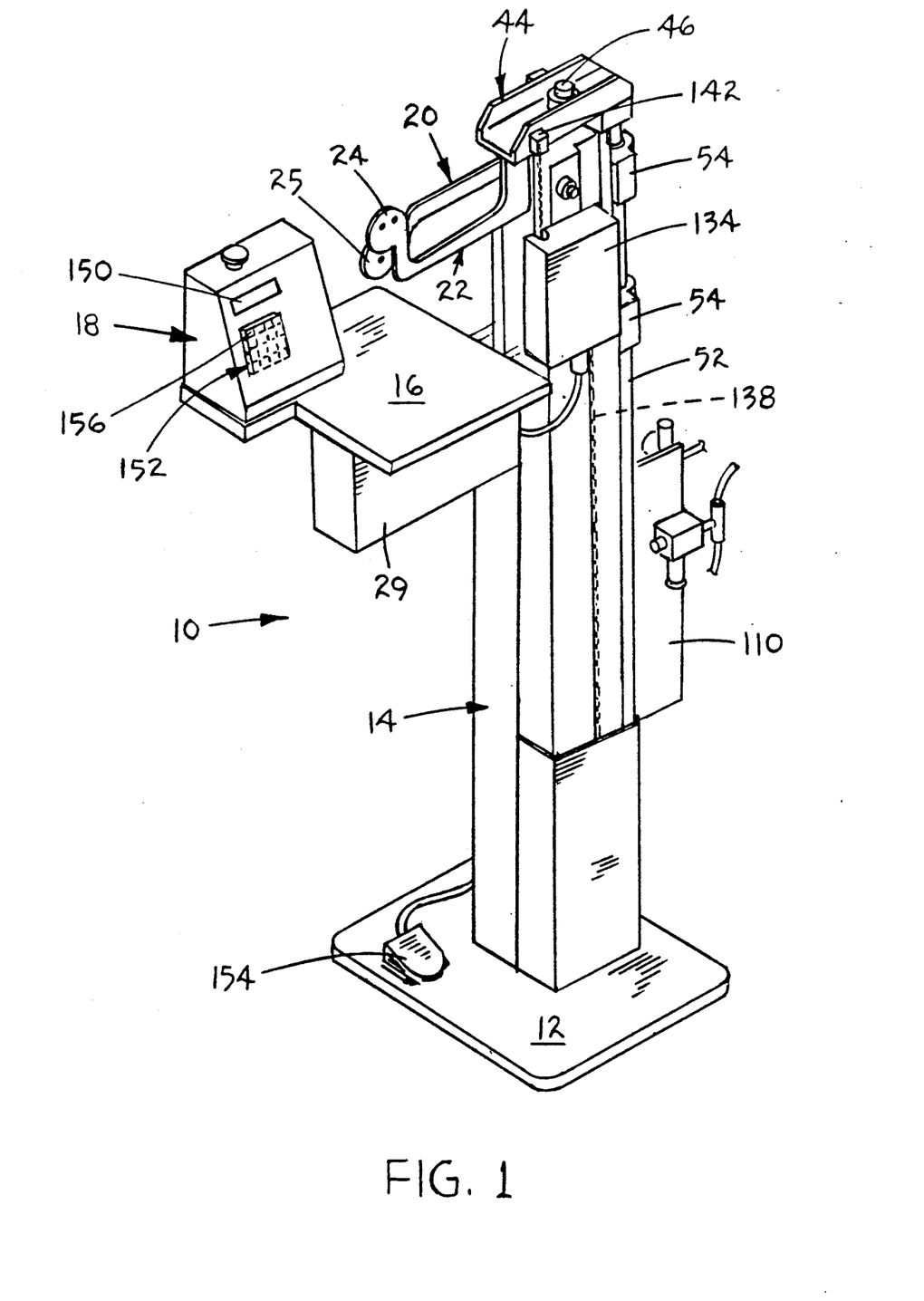
FIG. 1 is a perspective view of a testing mechanism according to the present invention.

Referring to the drawings, and initially to FIG. 1, the cross stretch machine 10 includes a support base 12, a vertically disposed support structure 14 secured to the base, a support table 16 secured to the vertical structure 14, and a controller 18 which includes a logic board. Extending generally horizontally at the upper end portion of structure 14 are arms 20 and 22, having a rounded hand portion 24 and 25, respectively, at the outer ends thereof for receiving thereover and applying a stretching force to a selected portion of an article to be tested.

Figure 4:
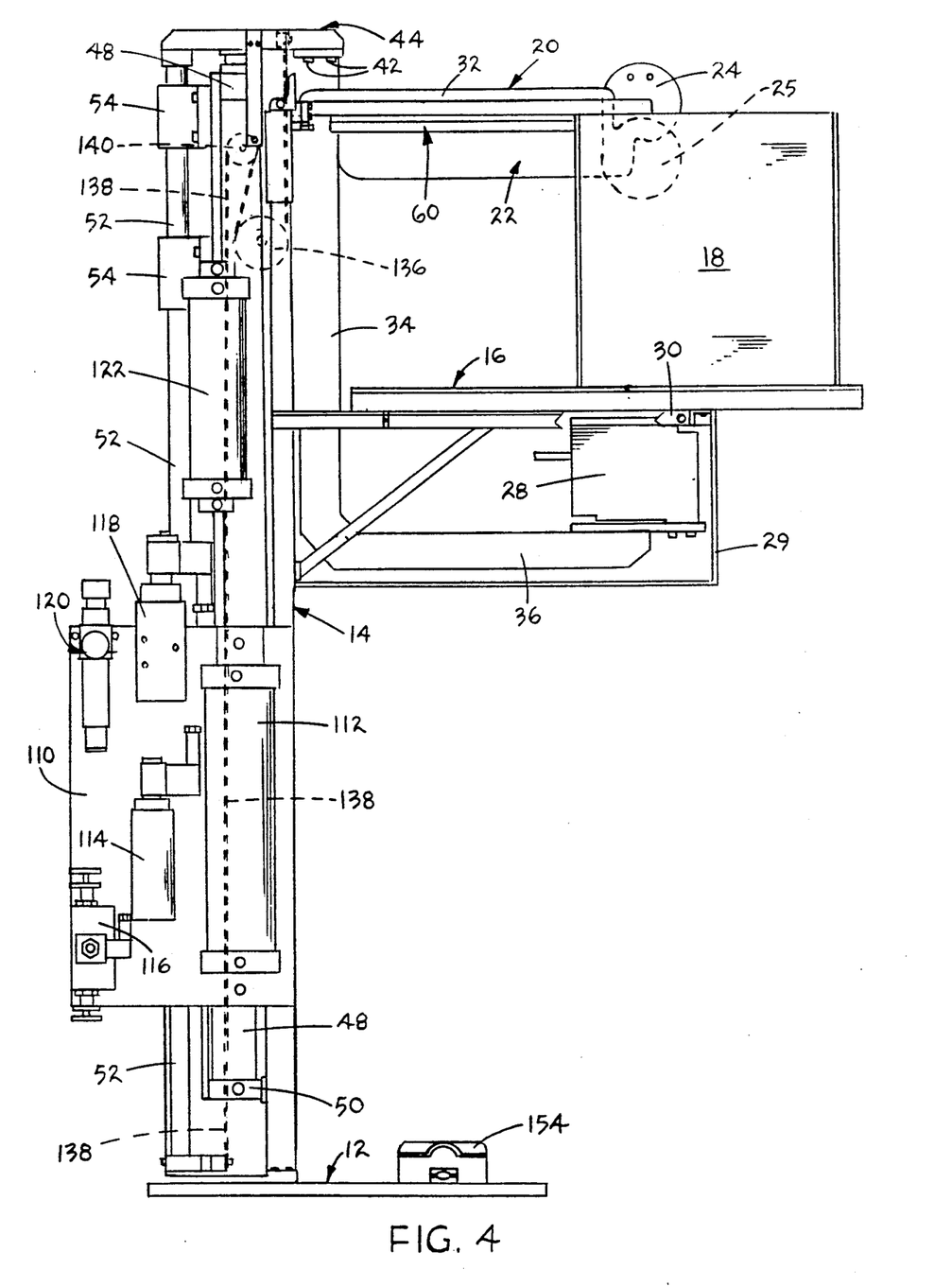
FIG. 4 is a rear elevational view of the mechanism with certain parts removed.

The arm 20, and the integral hand 25, FIGS. 1 and 4, is coupled to a load cell 28 which, in turn, is adjustably coupled by screws, now shown, to the table 16 through a mounting plate 30. The arm 20 is generally C-shaped, FIG. 4, having an upper horizontal section 32 having the hand 25 secured thereto, a vertical section 34 and a lower horizontal section 36 coupled to the load cell 28. The load cell is partially encompassed by a housing 29.

Figure 8:
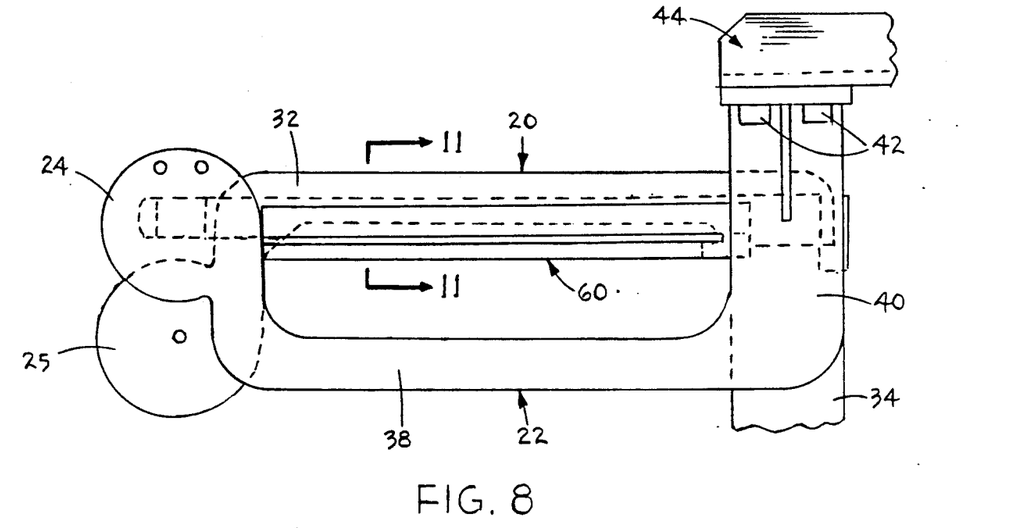
FIG. 8 is an enlarged fragmentary view of the arms and arm guard.

The arm 22, FIG. 8, includes a horizontally extending section 38, having the hand 24 attached thereto, and a vertical section 40 secured by fasteners 42 to a rod assembly 44. The rod assembly 44 is fixedly secured to the upper end of the rod 46 of an elongated fluid cylinder 48. The lower portion of the fluid cylinder is attached to a bracket 50, FIG. 4, which, in turn, is secured to the vertical support structure 14.

The hand portions 24,25 are generally parallel to each other and disposed in vertical planes. It is also to be noted that the uppermost peripheral portion of hand 24 is positioned higher than the upper peripheral surface of section 32 of arm 20 when the arm 22 is fully retracted by the cylinder 48. Similarly, the lower peripheral portions of hand 25 is positioned lower than the section 38 of arm 22.

A vertically disposed Thompson rod 52 has the upper end secured to the rod assembly 44 and extends through spaced brackets 54,54 attached to the vertical support structure 14. The rod 52 serves as an anti-rotation device for the cylinder rod 46 and arms 20,22 and also serves to take the lateral load off the end of the rod 46.

Figure 6:
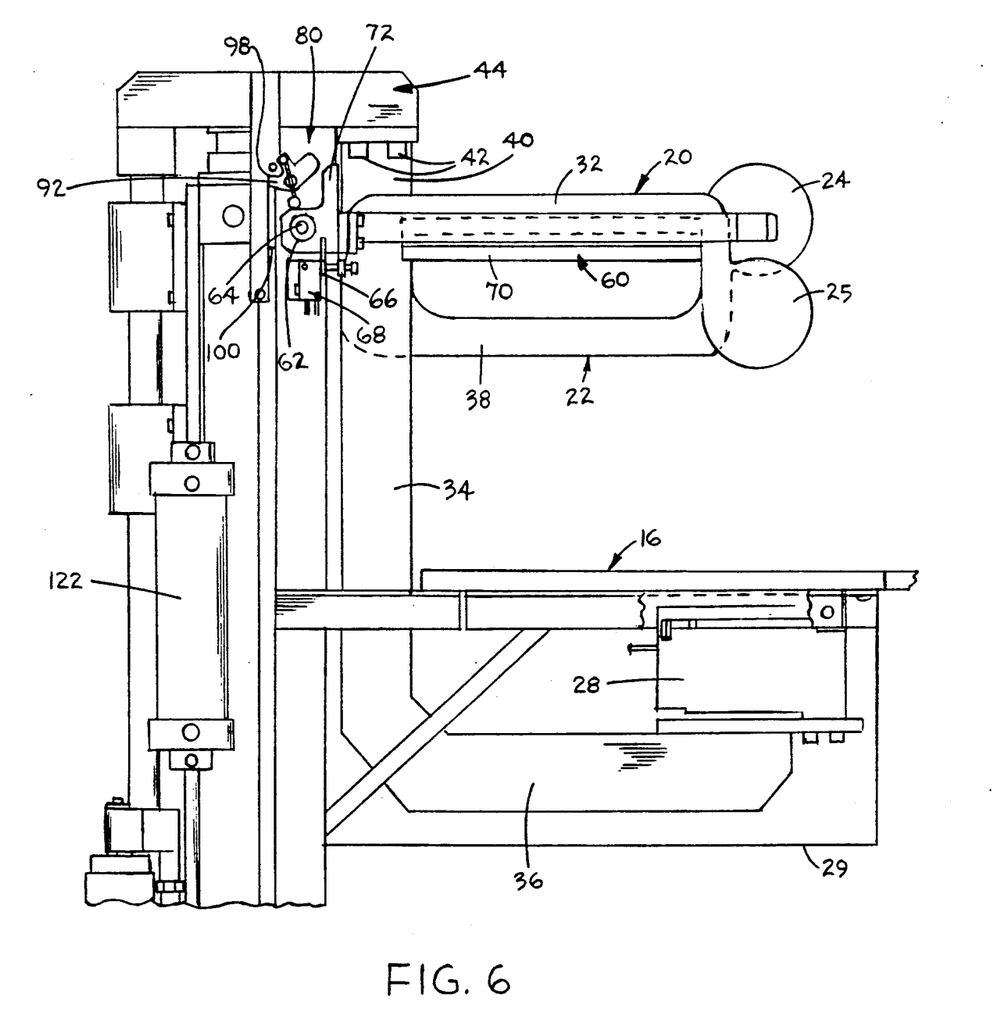
FIG. 6 is an enlarged view of the upper portion of the mechanism illustrating the arm assemblies and arm guard mechanism.
Figure 9:
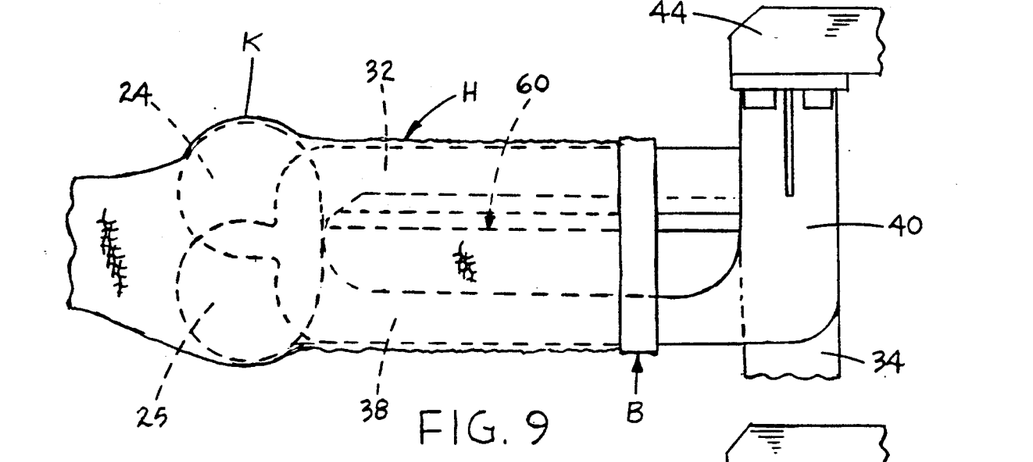
FIG. 9 is an elevational view of the arms in the collapsed position with a hosiery article placed thereon.
Figure 10:
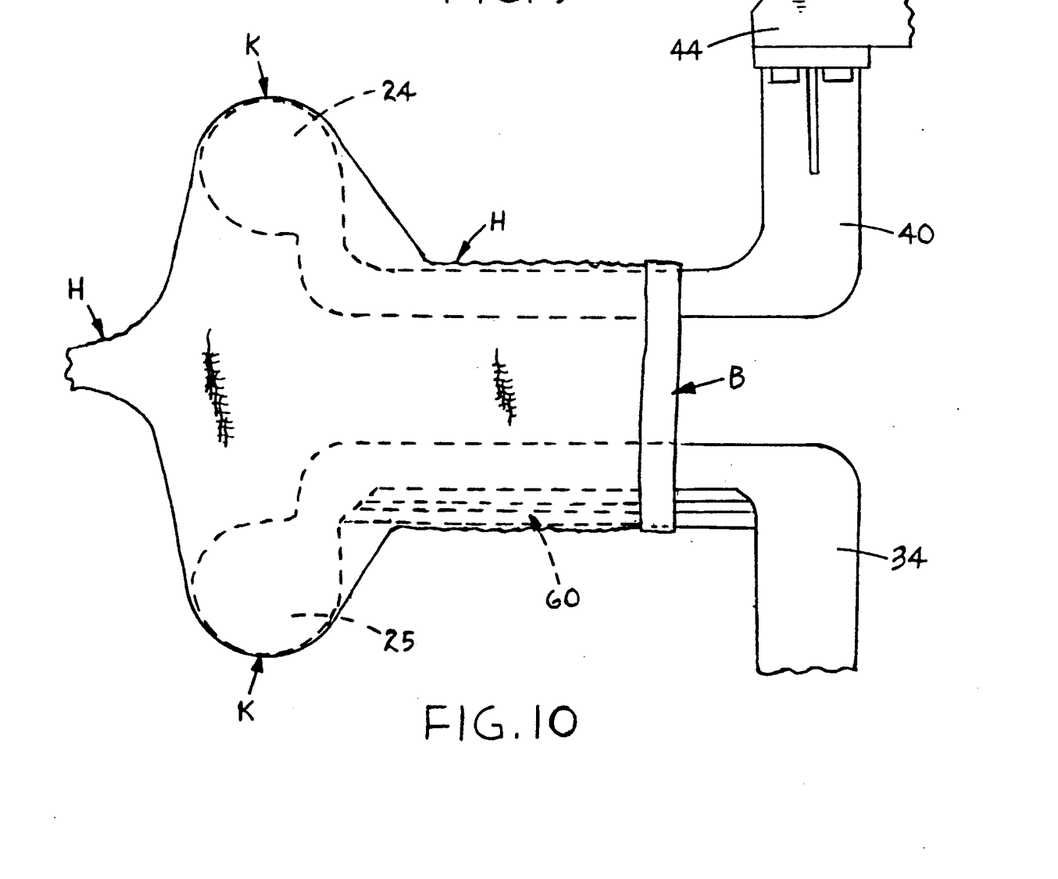
FIG. 10 is an elevational view of the arms applying a cross stretch to a selected portion of a hosiery article.
Figure 11:
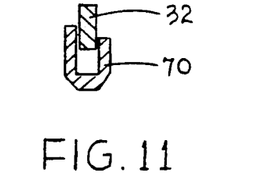
FIG. 11 is a cross-sectional view of the load cell arm and arm guard taken along line 11—11 of FIG. 8.
Figure 12:
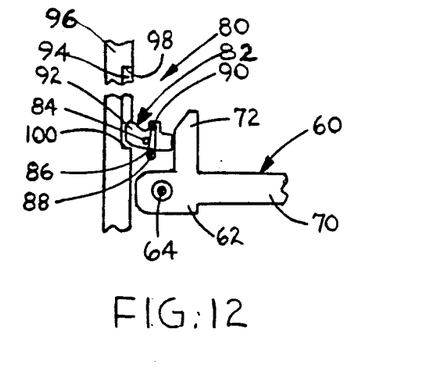
FIG. 12 is a fragmentary elevational view of the arm guard and latch assembly therefor.

An arm guard 60, FIGS. 6,8, is provided which serves as a safety device and also serves to shield portions of the hosiery article from section 32 of the load cell arm 20 in certain situations. For example, when the hosiery article H knee portion K. FIG. 9, is being tested and is properly positioned on the hands 24,25, the band B or panty portion extends around the arms 20,22 and without the arm guard 60 could apply a force directly to the arm section 32 and to the load cell 28 which would result in an incorrect reading. The arm guard 60 includes a portion 62, FIG. 6, having an opening therein for receiving a shaft 64, which is suppported by structure 14, thus permitting limited pivotable dislacement thereabout in a vertical plane. A plate 66 depends from the arm portion 62 and is adapted to actuate a switch 68 mounted on the vertical support structure 14. The arm guard 60 also includes an elongated portion 70 having a generally U-shaped cross-sectional configuration as shown in FIG. 11 which partially receives the lower portion of the horizontal section 32 of the load cell arm 20 to prevent portions of the hosiery article encompassing the arm sections 32,38 and not being tested from engaging the section 32 of arm 20 and affecting the load cell when a selected portion of the article being tested is positioned over the hands 24,25 and stretched due to displacement of the arm 22 connected to the rod 46 of cylinder 48. Thus, only forces applied directly by the article to the hands, and indirectly through the arms, to the load cell is detected by the load cell, and the arm guard 60 prevents portions of the article not being tested but extending around the arms from applying forces directly to the horizontal section 32 of arm 20 and to the load cell. The arm guard 60 also includes an upstanding portion 72 which cooperates with an arm guard latch toggle assembly 80. The assembly 80 includes a latch 82 pivotably mounted upon a pin 84 which is secured to the vertical support structure 14, and adapted to be urged in one direction or the other by an over-center spring 86 having one end secured to a fixed pin 88 supported by the vertical support structure 14 and the other end attached to a portion 90 of the latch 82. One end portion 92 of the latch is positioned within a groove 94 of a plate 96 displaceable with the cylinder rod 46 and rod assembly 44 and is capable of being moved to the FIG. 6 position by a shoulder 98 and to the FIG. 12 position by the shoulder 100.

Figure 2:
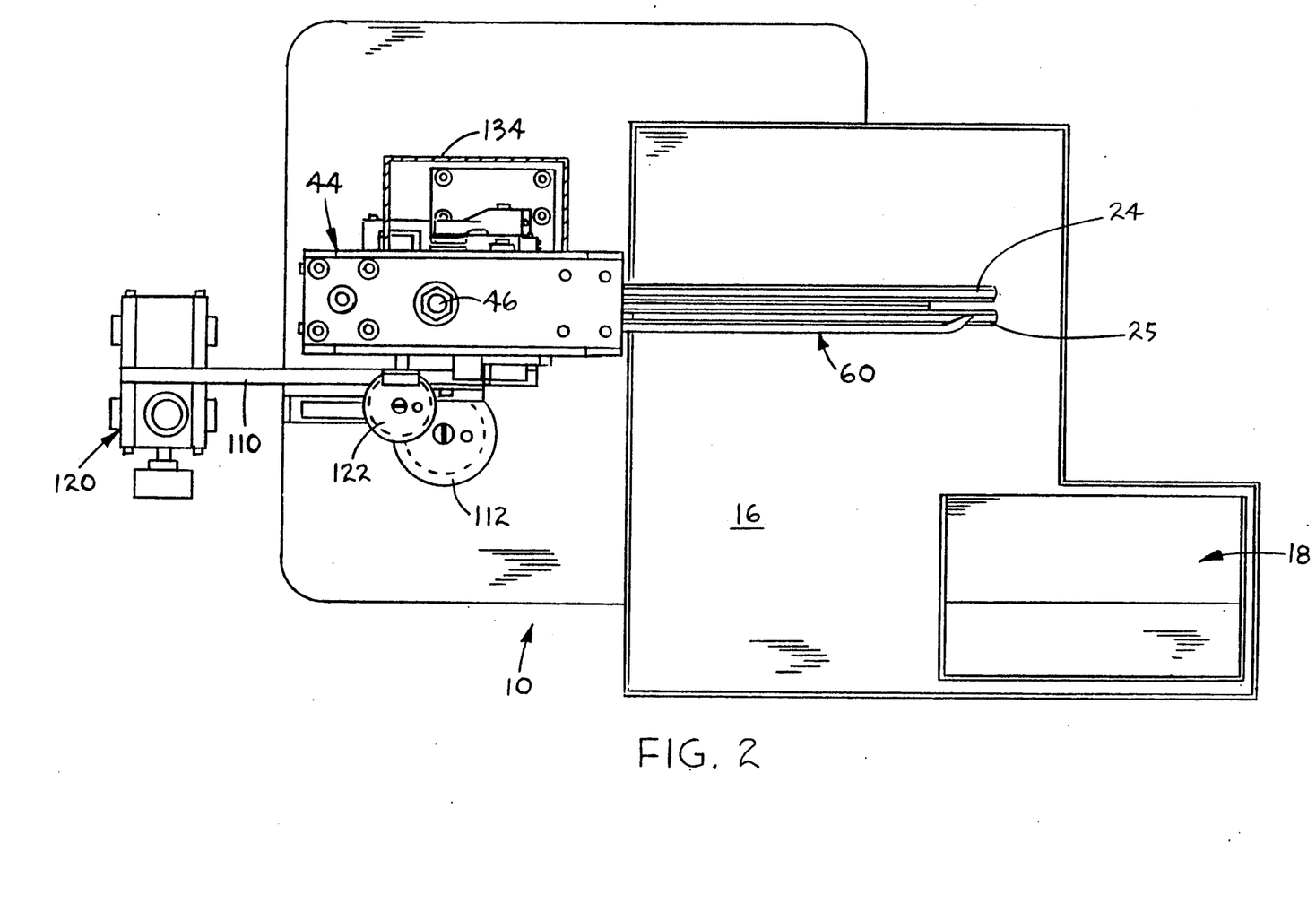
FIG. 2 is an enlarged top plan view of the mechanism of FIG. 1.
Figure 7:
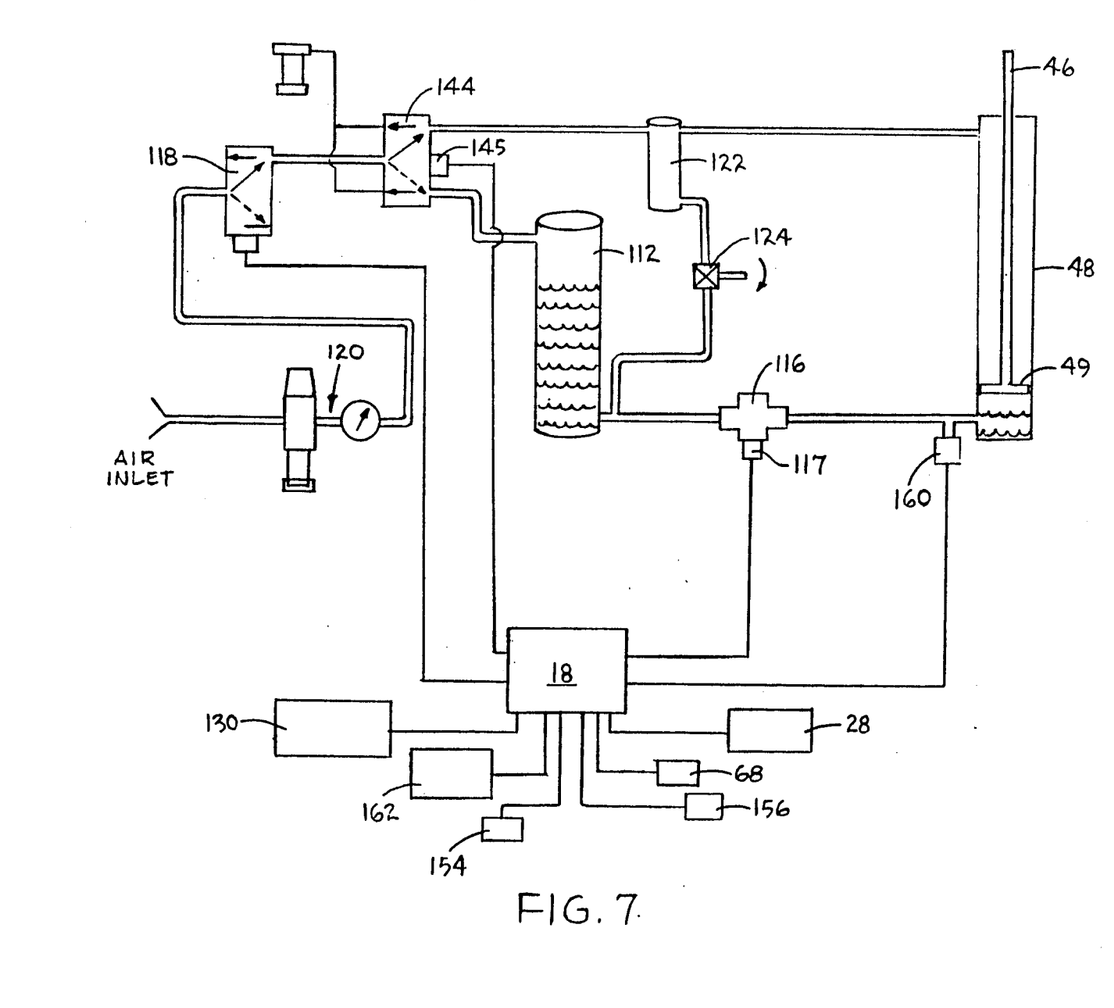
FIG. 7 is a schematic diagram illustrating various fluid and electrical components of the system.

As shown by FIGS. 1, 2 and 4, a plate 110 is provided for mounting various fluid components shown in FIG. 7. The plate 110 extends in a vertical plane and is fixed to the vertical support structure 14 by suitable fastening means. Mounted upon the plate 110 are a hydraulic fluid reservoir 112, a directional valve 114, a lock valve and flow controllers 116, a vent valve 118, and a pressure regulator and gauge 120. A blow-by tank 122 is located above the reservoir 112 and serves to catch the hydraulic fluid that escapes past the piston 49 of the cylinder 48. An hydraulic fluid return valve 124, FIG. 7, controls the flow of fluid from the tank 122 to the tank or reservoir 112.

The flow controls of the lock valve 116 regulate the rate of extension and retraction of the cylinder rod 46.

Under certain conditions the cylinder 48 can apply an excessive amount of force to the arm guard 60 thus damaging the arm guard and arm guard latch. Therefore a cylinder pressure switch 160, FIG. 7, is provided to detect the onset of an excessive force condition and signal the controller to take corrective action by reversing the direction of movement of the cylinder rod 46. The most common situation in which excessive force can be applied is the misloading of a test article so that the cylinder applies forces to the horizontal sections 32,38 of arm 20,22 but not to the arms through the hands 24,25. Since the load cell 28 feels only the force applied to the hands, and not by forces exerted on arm section 32 the cylinder will apply excessive force to the arms and the load cell will not be able to signal the controller 18 to reverse the direction of the cylinder rod 46.

Figures 3, 5:
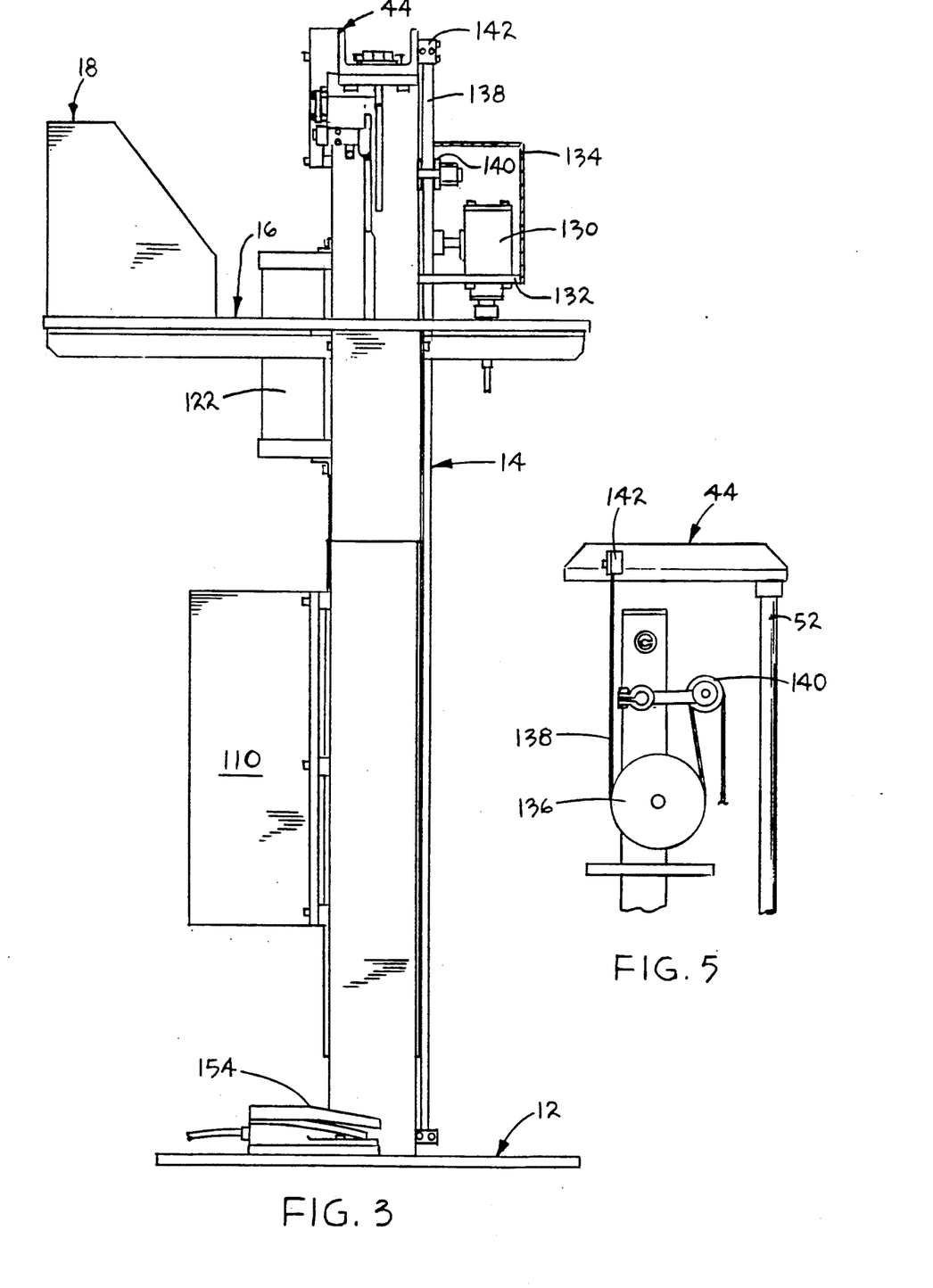
FIG. 3 is a fragmentary elevational view of the mechanism taken from the left side of FIG. 2.
FIG. 5 is an enlarged view of the uppermost portion of the mechanism illustrating the encoder drive pulley and belt.

An encoder 130, FIG. 3, is mounted upon a plate 132 which is fixed to the upright support structure 14. The encoder, which is encompassed by a cover 134, includes a pulley 136 over which is directed a toothed belt 138 as shown by FIGS. 3-5. The belt 138 also passes over a tensioner pulley 140. The upper end of the belt 138 is secured to a bracket 142 attached to the rod assembly 44 and the lower end is secured to a bracket 144 fixed to the lower end portion of the Thompson rod 52. Upon displacement of the belt 138, Thompson rod 52, and rod assembly 44 upwardly by the cylinder 48, the pulley 136, through shaft 146, drives the encoder which, in turn, feeds a signal to the controller 18.

In the operation of the system, a hosiery article or garment is pulled over the hands 24,25 until the portion of the garment to be tested is properly centered on the hands with the courses in the fabric being vertical.

After loading, the operator may choose to put some identifying information such as style number, machine number, etc. on the display 150 of the controller 18 by means of the keyboard 152.

The operator then starts the machine by actuating the step switch 154 or a start button 156 on the keyboard 152. Upon actuation of the start switch or button, the controller 18 actuates the valves 116,144,118 through solenoids 117,145,119 to a state to direct hydraulic fluid from the reservoir 112 to the lower portion of the cylinder 48 which starts moving the rod 46, Thompson rod 52, belt 138, and top shaft assembly 44 including the cylinder arm 22 upwardly. As the hand 24 starts moving upwardly relative to the hand 25, that portion of the garment being properly positioned thereon begins to stretch and a force is applied to the load cell 28 through the arm 20 by the hand 25. The load cell sends a signal to the controller 18 indicating the degree of pressure being applied to the hands 24,25 by the article portions centered thereover for measurement. At the same time, upward displacement of the belt 138 drives the encoder 130 which feeds a signal to the controller 18 indicating the distance the cylinder rod 46 has moved vertically upwardly. The system continues to extend and the controller records the distance and force values every two milliseconds.

The desired pressure applied to the load cell during a test sequence may vary. The controller 18 is programmed to direct a signal to solenoid 145 reversing the directional valve 144 and valve 116 and the cylinder rod 46 moves back to the home position once a predetermined pressure is reached. Typically, for testing hosiery articles, the desired test range is 9.5 to 10.5 pounds. When the desired force is applied to the load cell 28, for example, 9.5 pounds, a signal is directed to the controller 18 which, in turn, controls valves 144 and 116 through solenoids 145 and 117 to return the cylinder rod 46, rod assembly 44, Thompson rod 52, arm 22 and hand 24 back to the home positions. When the cylinder rod comes to rest the elongation of the article is shown on the controller display 152.

The controller 18 has several user programmable parameters. The machine may perform a group of tests on different areas of the same article, store the results until all areas have been tested, and then by incorporating a printer 162 with the system, print all test results for that article.

The arm guard 60 also serves as a safety mechanism. If an object is positioned between the arms 20,22, and a test initiated, the cylinder 48 moves the arm upwardly striking the object which, in turn, pivots the arm guard 60 slightly upwardly actuating the switch 68 which signals the controller 18 to reverse movement of the cylinder rod 46. Pivoting of the arm guard is possible since the toggle latch assembly 80 is in the FIG. 6 position. However, once the cylinder moves the plate upwardly sufficiently for the shoulder to move the toggle latch assembly 80 to the FIG. 12 position, the arm guard 60 cannot pivot.

What is claimed is:

1. In an apparatus for measuring cross stretch in a preselected section of an elongated hosiery article having a tubular portion, a support frame, a pair of relatively moveable arms mounted upon said support frame and adapted to receive thereover a hosiery article selected tubular section to be tested, means for displacing vertically a first arm of said pair of arms relative to a second arm of said pair of arms to stretch said hosiery article tubular section to be tested and positioned therearound, means for detecting when a predetermined force is applied by the stretched hosiery article tubular portion to be tested to said second arm upon actuation of said first arm displacement of said arms relative to each other, control means responsive to said means for detecting a predetermined force for recording the linear displacement of said pair of arms relative to each other for determining whether the cross stretch of the article in said preselected section falls within an acceptable range and for reversing said displacing means to relieve the force applied to the hosiery article, and means for preventing non-selected sections of said hosiery article extending around said arms from applying a force directly to said second arm upon displacement of said first arm to stretch said preselected section.

2. The apparatus as recited in claim 1, said means for detecting the predetermined force applied to said second arm including a load cell positioned intermediate said support means and said second arm.

3. The apparatus as recited in claim 1, wherein each of said arms of said pair of arms terminates in an arcuate portion for receiving therearound said preselected section of an article to be tested, the outermost opposed peripheral portions of which apply forces to inner peripheral portions of said preselected section of a hosiery article.

4. The apparatus as recited in claim 1, wherein said means for preventing non-selected sections of a hosiery article extending around said pair of from applying a force to said second arm includes guard means for shielding said second arm from non-selected sections of said hosiery article upon stretching of said preselected section.

5. The apparatus as recited in claim 4, said guard means including a guard arm mounted for limited pivotable displacement on said support frame and latch control means for selectively controlling said guard arm to prevent pivotable displacement upon vertical predetermined displacement upwardly by said first arm to stretch said hosiery article preselected section.

6. The apparatus as recited in claim 5, said guard means further including switch means connected to said control means, said latch control means permitting pivotable displacement of said guard arm to actuate said switch means, and said control means for deactivating said first arm displacement means if an object is positioned intermediate said first arm and said second arm upon displacement of said first arm.

7. The apparatus as recited in claim 1, wherein said means for displacing vertically said first arm including a fluid cylinder.

* * * * *